United States Patent
Marshall et al.

(10) Patent No.: US 7,223,259 B2
(45) Date of Patent: May 29, 2007

(54) SYRINGE HOLDERS

(75) Inventors: Jeremy Marshall, Oxford (GB); Steven Mark Guy Rolfe, Oxon (GB)

(73) Assignee: Owen Mumford Limited, Oxford (GB)

( * ) Notice: Subject to any disclaimer, the term of this patent is extended or adjusted under 35 U.S.C. 154(b) by 307 days.

(21) Appl. No.: 10/476,073

(22) PCT Filed: Apr. 29, 2002

(86) PCT No.: PCT/GB02/01955

§ 371 (c)(1),
(2), (4) Date: Oct. 28, 2003

(87) PCT Pub. No.: WO02/087670

PCT Pub. Date: Nov. 7, 2002

(65) Prior Publication Data

US 2004/0144668 A1    Jul. 29, 2004

(30) Foreign Application Priority Data

Apr. 28, 2001  (GB) ................. 0110443.9

(51) Int. Cl.
*A61M 5/32* (2006.01)
(52) U.S. Cl. ..................... 604/198; 604/192
(58) Field of Classification Search ............ 604/110, 604/195, 198, 197, 218, 222, 192
See application file for complete search history.

(56) References Cited

U.S. PATENT DOCUMENTS

| 4,723,943 | A | * | 2/1988 | Spencer ............... 604/198 |
| 4,923,447 | A | * | 5/1990 | Morgan ............... 604/198 |
| 4,950,265 | A | * | 8/1990 | Taylor ................. 606/1 |
| 5,300,041 | A | * | 4/1994 | Haber et al. ........... 604/207 |
| 5,562,626 | A | * | 10/1996 | Sanpietro ............. 604/110 |
| 5,743,887 | A | * | 4/1998 | Brattesani ............. 604/192 |
| 5,925,032 | A | * | 7/1999 | Clements ............... 606/1 |

FOREIGN PATENT DOCUMENTS

| DE | 199 40 097 | 3/2001 |
| WO | WO 99 17823 | 4/1999 |

* cited by examiner

*Primary Examiner*—Kevin C. Sirmons
*Assistant Examiner*—Benjamin Huh
(74) *Attorney, Agent, or Firm*—Young & Thompson

(57) ABSTRACT

A syringe holder is designed to be thrown away after a single use with the syringe safely captive within. The holder has a barrel (5) into whose rear end a syringe (1) is entered until the rear flange (2) of the syringe seats in a socket (15). Then a gate (16) is hinged in a radial plane through a slot (14) in a thick flange (12) surrounding the socket (15) and snap fastens in a position obstructing rearward movement of the syringe (1). The syringe needle (3) projects forwardly of the barrel and is shrouded by a sleeve (7) captive to the barrel and urged forwards by a spring (6).

11 Claims, 2 Drawing Sheets

Figure 1:
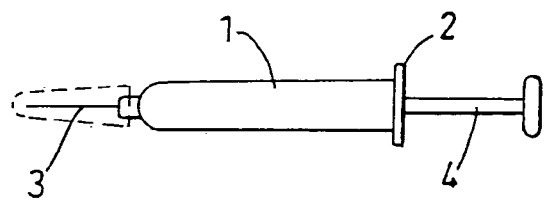

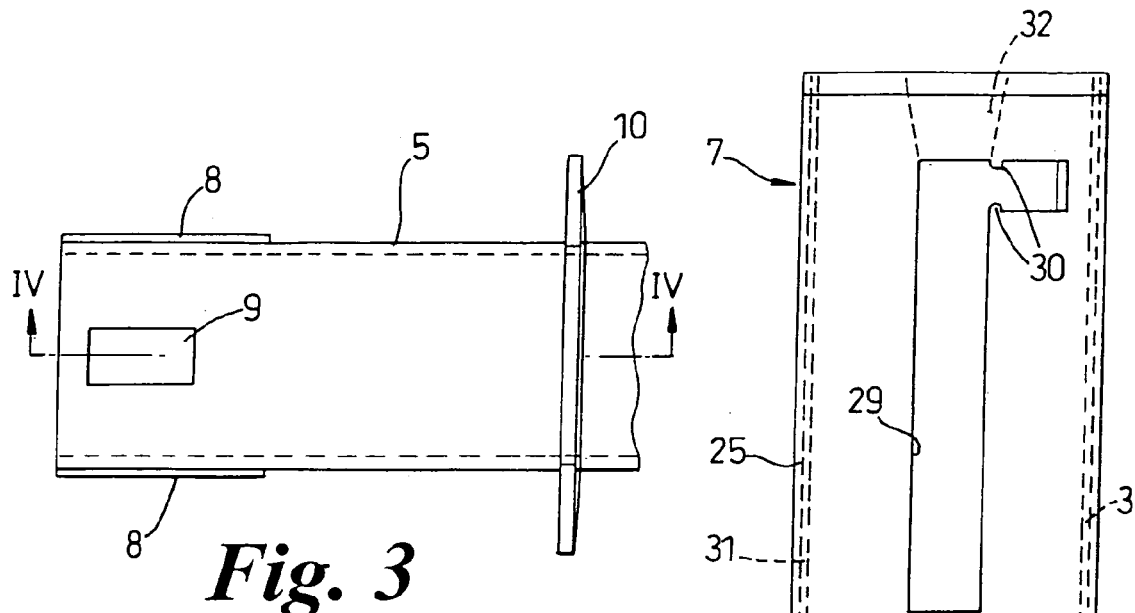
Fig. 3
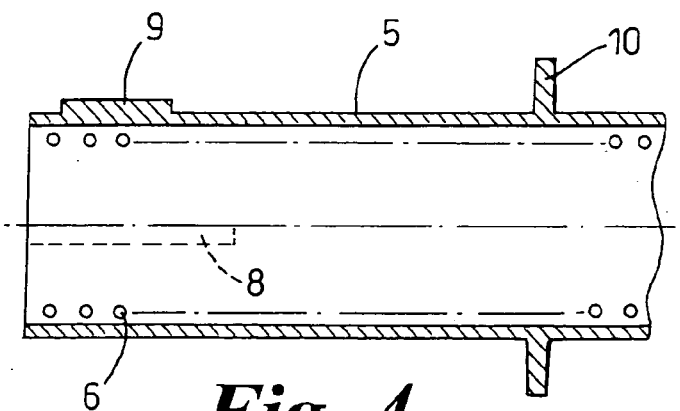
Fig. 4
Fig. 5
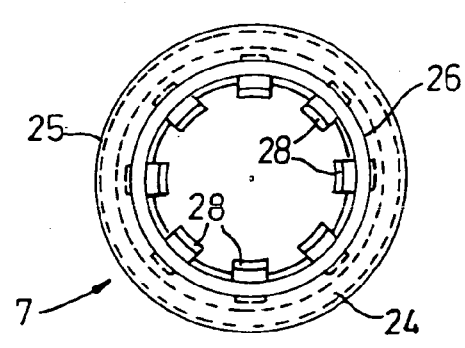
Fig. 6

SYRINGE HOLDERS

This application is a 371 of PCT/GB02/01955 filed on Apr. 29, 2002 which claims the benefit of foreign application UNITED KINGDOM 0110443.9 filed on Apr. 28, 2001.

This invention relates to syringe holders.

The syringe to be used with these holders will be of the usual form, with a cylindrical capsule containing the dose, which is captive by a plunger whose rod extends clear of the rear end of the capsule. That rear end has a radially projecting flange, usually annular with two flats, while a needle projects axially from the reduced forward end. A protective cap is generally provided to shield the needle before use. Such a syringe will be referred to as of the kind described.

Such syringes can be used by themselves, but they are small and "fiddly", and control is not easy. Also the exposed needle is dangerous and after use it is important to make it safe. Replacing the cap is not an answer, since it can easily be removed again.

Therefore devices have been developed to contain the syringe and to make it easier to use and to render it safe after use. Some of these are quite complex, with trigger release of a spring firing mechanism, and automatic spring retraction to bring the needle back into a housing. But they are not disposable items, or at least they are rather expensive to throw away after a single use, and they need to be carefully unloaded of their syringes.

The aim of this invention is to provide a basic throwaway holder, which is easy to load with a syringe, which makes the syringe secure when loaded, and which preferably also offers a simple and reliable way of irreversibly shrouding the needle after use.

According to the present invention there is provided a syringe holder comprising a barrel with an open rear end to receive a syringe of the kind described, said rear end having means engageable behind the flange at the rear end of the capsule once the syringe reaches its fully housed position, thereby to hold the capsule within the barrel, characterised in that the rear end of the barrel has a socket to receive and locate said flange and a gate that hinges in a radial plane from a non-obstructing position clear of the socket to an obstructing position preventing escape of the capsule flange from the socket but not impeding operation of the plunger, the gate being captive in said obstructing position.

The gate may be integrally moulded with the barrel and connect thereto by a thin web which acts as its hinge.

Preferably, the gate hinges through a slot to intrude into the socket, snap fastening therein as it reaches said obstructing position.

Additionally, a spring inside the barrel can surround the capsule of the syringe to act on a protective sleeve captive to but slidably engaged with the forward end of the barrel. This will urge the sleeve forwards to shroud the needle before and after use, but allow the sleeve to retract and expose the needle during the injection.

The engagement of the sleeve and barrel may permit mutual rotation about their common axis from a free sliding condition to an irreversibly locked condition when the sleeve is in its forward needle shrouding position. In this case the barrel conveniently has a projection that moves within an L-shaped slot in the sleeve, the long arm of the slot being longitudinal of the sleeve and the short arm circumferential towards its rear end. The co-operating cylindrical surfaces of the barrel and sleeve may have tooth-profiled splines that can snap past each other when the mutual rotation moves the projection into the short arm of the slot. The projection is thereby trapped and axial movement is prevented.

Alternatively, or in addition, the projection may have an irreversible snap-in engagement with the short arm of the slot.

The sleeve may also have another function, being equipped internally with integral spring tabs angled to be pulled back past the base of a needle cap or sheath, but then flexing inwards so that, when the sleeve is urged forwards again, the tabs push the cap or sheath off the needle while the sleeve assumes its needle-protecting position.

Figure 2:
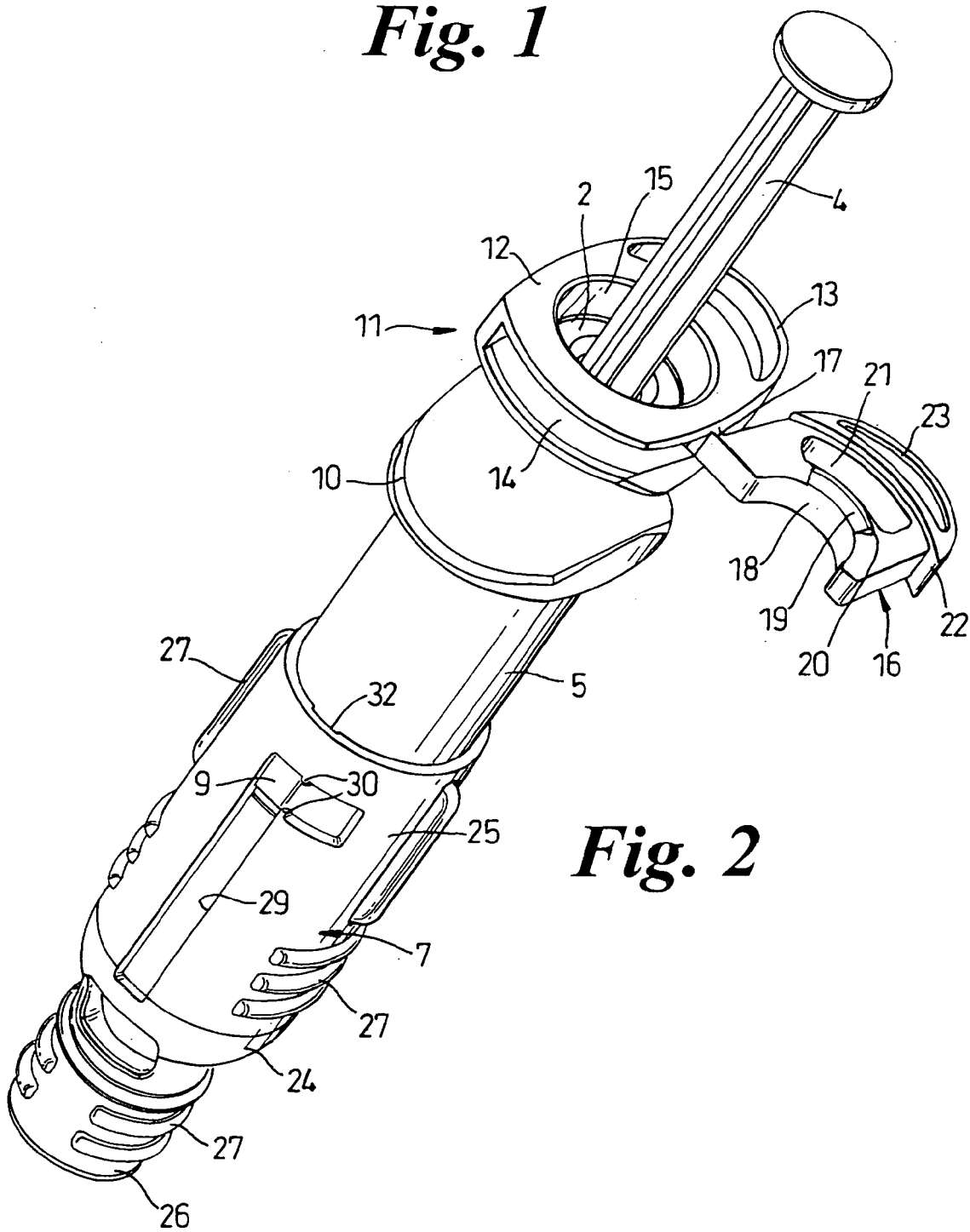

For a better understanding of the invention, one embodiment will now be described, by way of example, with reference to the accompanying drawings, in which:

FIG. 1 is a side view of a medical syringe,
FIG. 2 is a perspective view of a syringe holder,
FIG. 3 is a side view of part of a barrel of the syringe holder,
FIG. 4 is a section on the line IV—IV of FIG. 3,
FIG. 5 is a side view, partly in ghost, of a needle protector sleeve of the syringe holder, and
FIG. 6 is an end view of the sleeve, in the direction A of FIG. 5.

The syringe to be used in the holder is of the usual form, having a capsule 1 with an outward radial flange 2 at its rear end. A needle 3, initially with a cap shown in outline, projects from its forward end, and a plunger 4 projecting from the rear end is urged forwards in use to express a dose within the capsule through the needle 3.

The holder has three main components, namely a barrel 5, a helical spring 6 within the barrel, and a needle protection sleeve 7 which telescopes over the forward end of the barrel.

The barrel 5 is straight cylindrical over most of its length. At its forward end there are two diametrically opposed external splines 8 of right-angled triangular cross-section, aligned parallel with the axis of the barrel, and with one side radial to the barrel and the other almost tangential thereto. Both radial sides face in the same circumferential direction. Midway between these splines 8 on the outer surface of the barrel and set back a bit from the end is a shallow square projection 9.

About two thirds the length of the barrel back from its forward end there is a generally elliptical external flange 10, for ease of handling the device in use.

The barrel has an asymmetric cup formation 11 at its rear end to receive and locate the rear end of the syringe. A flange 12 is thick and is extended radially over an arc of about 90° by a curved loop 13. Opposite this, a slot 14 is provided between the upper and lower faces of the flange 12, open to the socket 15 in which the flange 2 of the syringe seats. When that is properly in position, the rear face of the flange 2 is just beyond the slot 14 in the forwards direction. A gate 16 is hinged by a thin web 17 to the side of the flange 12 and 90° from the crown of the loop 13 and can be swung from the retracted position shown to enter and become captive in the slot 14, at the same time making the syringe captive in the barrel 5. The gate is generally D-shaped with the hinge at one corner, but the straight part of the D has a semicircular cut-out 18 which allows it to half-surround the plunger 4 while the adjacent part of the body of the gate overlies the flange 2 and blocks rearward movement of the syringe.

The gate 16 snap fastens in the slot 14. It is largely of a thickness equal to the width of the slot 14, but around the crown of the cut-out 18 there is a correspondingly curved ramp 19 ending in a step 20 back to the main body of the gate. As that is closed, the ramp wedges the slot 14 a bit wider, but once the step 20 reaches the socket 15 the slot 14 closes against the gate and that is secure.

Beyond the ramp 19 from the cut-out 18 there is a curved slot 21, and beyond that the gate steps out into a thicker section 22 with a loop 23 so that, when closed, there is a match with the diametrically opposite loop 13.

The needle protector sleeve 7 is a cylindrical member reducing at a shoulder 24 forward of its mid-length. Both the larger and the reduced diameter portions 25 and 26 have external ribs 27 for a good grip. Internally, there are tabs 28 projecting inwardly and forwardly from the shoulder 24, which is stepped on the inside rather than sloping as on the outside. The larger diameter portion 25 has an L-shaped slot 29 with the long arm extending over most of its length, and the short arm being part circumferential at the rear end. The basic width corresponds to that of the projection 9, and at the entrance to the short arm there are small lugs 30 which make for a snap action entry of the projection 9 into that part of the slot. Two diametrically opposed splines 31 are formed internally of the larger diameter portion 25 and are positioned to co-operate with the splines 8 when the projection 9 enters the short arm of the slot 29.

The device is assembled by inserting the spring 6 into the forward end of the barrel 5 and then pressing that forward end into the rear portion of the protector sleeve 7 with the projection 9 aligned with the long arm of the slot 29. There is enough flexibility and resilience for this to be a snap action, and to ease the fitting there is a shallow longitudinal channel 32 on the inside of the sleeve from its rear end to the slot 29 to accommodate the projection 9 to some extent, although it will still have to be forced through. Once the projection 9 is in the slot 29 the two members 5 and 7 are mutually captive. The holder is then ready to receive the syringe, which is entered into the rear of the barrel 5 until its flange 2 seats in the socket 15, to be trapped as described.

Prior to use, the protector sleeve 7 is moved rearwardly against the spring 6, which bears on the inner step in the shoulder 24, until the tabs 28 snap past the enlarged rear end of the needle cap. When the sleeve 7 is let go, it is moved forwards again by the spring 6 and the tabs 28 ease the needle cap off. But when that cap is removed the tip of the needle 3 remains shrouded by the reduced diameter portion 26. The device is now ready to use.

The forward end of the sleeve 7 is applied to the patient's skin and pressure is exerted. The needle 3 penetrates as the sleeve 7 is pushed back. The amount the needle 3 projects is dependent on the length of the portion 26 of the sleeve 7 and the stop provided by the outer step in the shoulder 24, up against which the end of the barrel 5 comes. The projection 9 meets the forward end of the slot 29 at the same time. The spring 6, whose forward end abuts the inner step in the shoulder 24, is compressed. The plunger 4 is then pressed to eject the dose through the needle 3.

On withdrawal, the spring 6 exerts itself and pushes the sleeve 7 forwards so that the needle 3 is shrouded. The sleeve 7 is then pulled right forwards, if not already moved there by spring action, and twisted so that the projection 9 enters the short arm of the slot 29. As it seats, the splines 8 and 18 snap past each other, capturing the sleeve 7 in that position. So the needle 3 is not re-exposable, and the device is safe for disposal.

The snap action of the splines 8 and 18 is more positive than that of the projection 9 past the lugs 30, which could be omitted. Alternatively or in addition they could be made non-return in relation to the projection 9, rendering the splines 8 and 18 redundant or complementing those splines.

The invention claimed is:

1. A syringe holder for receiving a syringe having a cylindrical capsule containing a dose which is captive by a plunger whose rod extends clear of the rear end of the capsule, the rear end of the capsule having a radially projecting flange, said syringe holder comprising a barrel with an open rear end shaped to receive a syringe, said rear end having means engageable behind the flange at the rear end of the capsule once the syringe reaches its fully housed position, thereby to hold the capsule within the barrel, wherein the rear end of the barrel having a socket to receive and locate said flange and a gate that hinges in a radial plane from a non-obstructing position clear of the socket to an obstructing position, the syringe holder having a spring inside the barrel which surrounds the capsule of the syringe and acts on a protective sleeve captive to but slidably engaged with a forward end of the barrel, thus urging the sleeve forwards to shroud a needle of the syringe before and after use of the syringe, but allowing the sleeve to retract and expose the needle during use of the syringe preventing escape of the capsule flange from the socket but not impeding operation of the plunger, the gate being captive in said obstructing position,
   wherein the engagement of the sleeve and barrel permits mutual rotation about their common axis from a free sliding condition to an irreversibly locked condition when the sleeve is in a forward needle shrouding position,
   wherein the barrel has a projection that moves within an L-shaped slot in the sleeve, the long arm of the slot being longitudinal of the sleeve and the short arm circumferential towards its rear end, and
   wherein co-operating cylindrical surfaces of the barrel and sleeve have tooth-profiled splines that snap past each other when the mutual rotation moves the projection into the short arm of the slot, the projection thereby being trapped and axial movement prevented.

2. The syringe holder as claimed in claim 1, wherein the sleeve is equipped internally with integral spring tabs angled to be pulled back past the base of a needle cap or sheath, but then flexing inwards so that, when the sleeve is urged forward again, the tabs push the cap or sheath off the needle while the sleeve assumes its needle-protecting position.

3. The syringe holder as claimed in claim 1, wherein the gate is integrally moulded with the barrel and connects thereto by a thin web which acts as its hinge.

4. The syringe holder as claimed in claim 3, wherein the gate hinges through a slot to intrude into the socket, snap fastening therein as it reaches said obstructing position.

5. The syringe holder as claimed in claim 3, wherein a spring inside the barrel surrounds the capsule of the syringe to act on a protective sleeve captive to but slidably engaged with the forward end of the barrel, thus urging the sleeve forwards to shroud the needle before and after use, but allowing the sleeve to retract and expose the needle during the injection.

6. The syringe holder as claimed in claim 1, wherein the gate hinges through a slot to intrude into the socket, snap fastening therein as it reaches said obstructing position.

7. The syringe holder as claimed in claim 6, a spring inside the barrel surrounds the capsule of the syringe to act on a protective sleeve captive to but slidably engaged with the forward end of the barrel, thus urging the sleeve forwards to shroud the needle before and after use, but allowing the sleeve to retract and expose the needle during the injection.

8. The syringe holder as claimed in claim 3, wherein the projection has an irreversible snap-in engagement with the short arm of the slot.

9. The syringe holder as claimed in claim 1, wherein the projection has an irreversible snap-in engagement with the short arm of the slot.

10. The syringe holder as claimed in claim 9, wherein the sleeve is equipped internally with integral spring tabs angled to be pulled back past the base of a needle cap or sheath, but then flexing inwards so that, when the sleeve is urged forwards again, the tabs push the cap or sheath off the needle while the sleeve assumes its needle-protecting position.

11. A syringe holder for receiving a syringe having a cylindrical capsule containing a dose which is captive by a plunger whose rod extends clear of the rear end of the capsule, the rear end of the capsule having a radially projecting flange, said syringe holder comprising a barrel with an open rear end shaped to receive a syringe, said rear end having means engageable behind the flange at the rear end of the capsule once the syringe reaches its fully housed position, thereby to hold the capsule within the barrel, wherein the rear end of the barrel having a socket to receive and locate said flange and a gate that hinges in a radial plane from a non-obstructing position clear of the socket to an obstructing position, the syringe holder having a spring inside the barrel which surrounds the capsule of the syringe and acts on a protective sleeve captive to but slidably engaged with a forward end of the barrel, thus urging the sleeve forwards to shroud a needle of the syringe before and after use of the syringe, but allowing the sleeve to retract and expose the needle during use of the syringe preventing escape of the capsule flange from the socket but not impeding operation of the plunger, the gate being captive in said obstructing position, wherein the sleeve is equipped internally with integral spring tabs angled to be pulled back past the base of a needle cap or sheath, but then flexing inwards so that, when the sleeve is urged forwards again, the tabs push the cap or sheath off the needle while the sleeve assumes its needle-protecting position.

* * * * *